(12) United States Patent
Daftary et al.

(10) Patent No.: US 7,199,111 B2
(45) Date of Patent: Apr. 3, 2007

(54) AQUEOUS IFOSFAMIDE COMPOSITIONS FOR PARENTERAL ADMINISTRATION AND A PROCESS FOR THEIR PREPARATIONS

(75) Inventors: Gautam Vinod Daftary, Thane (IN); Srikanth Annappa Pai, Thane (IN); Sangeeta Hanurmesh Rivankar, Thane (IN); Praveen Kumar Subbappa, Thane (IN)

(73) Assignee: Bharat Serums & Vaccines Ltd., Maharashtra (IN)

( * ) Notice: Subject to any disclaimer, the term of this patent is extended or adjusted under 35 U.S.C. 154(b) by 508 days.

(21) Appl. No.: 10/724,638

(22) Filed: Dec. 2, 2003

(65) Prior Publication Data

US 2004/0186074 A1 Sep. 23, 2004

(30) Foreign Application Priority Data

Feb. 12, 2002 (IN) .................. 785/MUM/2002

(51) Int. Cl.
*A61K 31/724* (2006.01)
*A61K 31/664* (2006.01)

(52) U.S. Cl. ................. 514/58; 514/90; 514/110

(58) Field of Classification Search ............ 514/58, 514/90, 110
See application file for complete search history.

(56) References Cited

U.S. PATENT DOCUMENTS

| 4,727,064 A | 2/1988 | Pitha |
| 4,879,286 A | 11/1989 | Alam et al. |
| 4,952,575 A | 8/1990 | Sauerbier et al. |
| 5,158,779 A | 10/1992 | Gergely et al. |
| 5,227,373 A | 7/1993 | Alexander et al. |
| 6,407,079 B1 | 6/2002 | Müller et al. |

FOREIGN PATENT DOCUMENTS

| WO | WO 99/18973 | 4/1999 |
| WO | WO 02/02125 | 1/2002 |
| WO | WO 03/051297 A2 | 6/2003 |

OTHER PUBLICATIONS

Cheung, B.W.Y., et al., "Brain delivery of carbamazepine during intravenous administration of polyethylene glycol and 2-hydroxy-propyl-β-cyclodextrin formulations", STP Pharma.

*Primary Examiner*—Leigh C. Maier
(74) *Attorney, Agent, or Firm*—Kenyon & Kenyon LLP

(57) ABSTRACT

The present invention provides aqueous Ifosfamide compositions and a process for their preparation, in which the compositions have a reduced toxicity over and above the concomitant use of the uroprotective agent, Mesna. Aqueous Ifosfamide compositions can be prepared at concentrations as high has 1,1000 mg/ml.

38 Claims, No Drawings

AQUEOUS IFOSFAMIDE COMPOSITIONS FOR PARENTERAL ADMINISTRATION AND A PROCESS FOR THEIR PREPARATIONS

RELATED APPLICATIONS

This application claims priority to Indian Provisional Application Number 785/mum/02 filed Dec. 2, 2002; and Indian Application Number PCT/IN2003/000376, filed Dec. 2, 2003, all of which are herein incorporated in their entirety.

FIELD OF THE INVENTION

This invention relates to aqueous Ifosfamide compositions comprising 2-hydroxypropyl-β-cyclodextrin (referred to hereinafter as "HPBCD"), which are suitable for parenteral use. This invention particularly relates to stable, clear, aqueous, ready to use, as well as concentrated, Ifosfamide compositions having reduced toxicity, as well as methods for their preparation.

BACKGROUND OF THE INVENTION

Two main groups of drugs used in the treatment of malignant disease are alkalyting agents and the antimetabolites. Ifosfamide is one of the widely used antineoplastic drug belonging to the alkalyting agents group.

Ifosfamide is chemically 3-(2-chloroethyl)-2-[(2-chloroethyl)amino]-tetrahydro-2H-1,3,2-oxazaphosphorin-2-oxide and is represented by the formula:

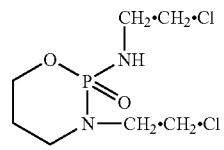

Ifosfamide is a white crystalline hygroscopic powder having a low melting point of 40° C. The powder has a water solubility of about 100 mg/ml.

Ifosfamide is used in the treatment of a variety of solid tumours including those of the cervix, endometrium, lung, ovary, testes and thymus as well as in sarcoma and in the treatment of Burkitts lymphoma. However, the treatment with Ifosfamide is associated with serious side effects such as haemorrhagic cystitis, myelosuppression, cardiac arrythmias, CNS disturbances, nephrotoxicity, haematological and gastro-intestinal reactions. The $LD_{50}$ in mouse on intravenous administration has been reported to be 338 mg/kg body weight. Combination with the uroprotective agent, mesna, reduces the incidence of hamorrhagic cystitis. Thus, mesna is normally administered intravenously at a dose of 20% of the Ifosfamide dose at time zero (the time of administration of Ifosfamide), and then at 4 and 8 hours.

Typically, Ifosfamide is given intravenously either by injection or by infusion as a diluted solution containing less than 4% w/v of Ifosfamide. Ifosfamide is very susceptible to hydrolytic degradation and accordingly prompt administration of such solutions is generally required. Therefore, commercially it is predominately available in dry form and is supplied as sterile packaged dry powder for dissolution in water for injection prior to administration. However, the low melting point and the hygroscopic nature of Ifosfamide make it necessary to fill the powder with great care accurately controlling both temperature and humidity to achieve a sterile product. Further, prolonged storage of the dry powder also results in sintering and yellowing, which in turn leads to a reduction in dissolution rate thereby increasing the time necessary for reconstitution.

To overcome difficulties associated with the thermal and hydrolytic susceptibility, lyophilization of the drug has been attempted. However, the lyophilization process is quite time consuming and requires specialized equipment. Personnel exposure to the strongly cytotoxic Ifosfamide occurring during reconstitution of lyophilized powder is also very undesirable.

Hence, others have attempted to obtain a clear liquid Ifosfamide compositions, suitable for parenteral administration, that are stable over a period of time U.S. Pat. No. 4,952,575 discloses preparation of an ethanolic solution of Ifosfamide containing 96% to 100% ethanol. Even though the degradation of Ifosfamide has been shown to be minimal, use of solvents in such a high concentration leads to other problems such as volatility, handling during manufacturing, and miscibility with blood on administration. As such, alcohol is pharmacologically active, which may also effect the person on administration of alcoholic solution of Ifosfamide.

U.S. Pat. No. 4,879,286 discloses a Cyclophosphamide formulated in a ready-to-dilute solution. The solution has organic polyols, namely propylene glycol and polyethylene glycol and their mixtures, as a solvent and also 0 to 50% water. The water may be partly replaced by 10 to 30% of ethanol.

WO 02/02125 discloses a liquid pharmaceutical composition for parenteral administration comprising Ifosfamide, solvent and optionally, conventional pharmaceutical carriers and excipients. According to the application, the solvent comprises 35–75% lower alcohol and 25–65% polyol. While lower alcohol solvent is usually ethanol, the polyol solvent is propylene glycol, glycerol and/or polyethylene glycol.

In both the U.S. Pat. No. 4,879,286 and WO 02/02125, the parenteral administration of larger amounts of polyols and alcohols lead to other problems like pain or irritation on injection, hemolysis, ototoxicity, cardiovascular effects, CNS effects and seizures. It may also lead to hyperosmolarity and lactic acidosis in patients with renal impairment.

WO 99/18973 describes a stable, ready-to-use liquor of Ifosfamide using Sodium chloride as a stabilizing agent. The invention also describes 10–500 mg/ml Ifosfamide composition containing Urea, sodium chloride and sodium dihydrogen phosphate. The compositions of the invention are said to be stable but there is no mention about the safety and toxicity of the composition. The higher concentration of urea in the formulation may lead to complications like hemolysis, irritation, phlebitis & thrombosis at the site of injection, and elevated blood ammonia & urea concentrations in patients with hepatic and renal function impairment.

WO 03/051297A2 describes a ready-to-use aqueous composition of Ifosfamide comprising 40–400 mM (10–100 mg/ml) of Ifosfamide in a pharmaceutically acceptable buffer. The patent suggests the use of buffers preferably from the group of $Na_2HPO_4$ and $NaH_2PO_4$ and $K_2HPO_4$ and $KH_2PO_4$. There is no report on the toxicity of Ifosfamide compositions disclosed in this patent.

Thus, there remains a need for a stable, concentrated Ifosfamide solution to facilitate handling during administration. In addition, there remains a need for Ifosfamide pharmaceutical compositions that exhibit less toxicity than the currently available compositions. The present invention meets this need.

SUMMARY OF THE INVENTION

The present invention provides aqueous compositions comprising Ifosfamide and 2-hydroxylpropyl-β-cyclodextrin. Preferably the Ifosfamide is present at a concentration up to 1,100 mg/ml. Other preferred Ifosfamide concentration ranges include 1–200 mg/ml; 10–100 mg/ml; 40–50 mg/ml; 200–500 mg/ml; 500–1,000 mg/ml; and greater than 1,000 mg/ml.

In aqueous compositions of the present invention, the 2-hydroxypropyl-β-cyclodextrin has a varying range of molar substitution by hydroxy propyl groups, including 0.05–2; 0.3–1.5; and 0.5–1.2.

In aqueous compositions of the present invention, the molar ratio of Ifosfamide to 2-hydroxypropyl-β-cyclodextrin is preferably 100:0.1–1:300; or 100:0.25–1:100; or 100:1–1:20; or 100:3.3–1:2.5.

The compositions of the present invention may further comprise pharmaceutically acceptable buffers, tonicity agents, preservatives, chelating agents, antioxidants, and/or anti-crystallizing agents.

Preferably the compositions of the present invention have a pH between 3.0–9.0 More preferably, between 5.0–8.0.

Suitable buffering agents include, but are not limited to, Sodium dihydrogen phosphate, Disodium hydrogen phosphate, Dipotassium hydrogen phosphate, Potassium dihydrogen phosphate, Histidine HCl, Sodium Hydroxide, Phosphoric acid, and Hydrochloric acid and mixtures thereof. A preferred buffering agent is a mixture of Sodium dihydrogen phosphate and Disodium hydrogen phosphate.

The present invention also provides process for the preparation of Ifosfamide compositions, whereby Ifosfamide is brought in intimate contact with 2-hydroxypropyl-β-cyclodextrin in water to form a Ifosfamide/2-hydroxyl-β-cyclodextrin solution. The Ifosfamide may be present in a concentration up to 1,100 mg/ml. Exemplary concentrations of Ifosfamide include 1–200 mg/ml; 10–100 mg/ml; 40–50 mg/ml; 200–500 mg/ml; 500–1,000 mg/ml; and greater than 1,000 mg/ml.

The 2-hydroxypropyl-β-cyclodextrin has a preferable molar substitution as described in the compositions of the present invention.

The molar ratio of Ifosfamide to 2-hydroxypropyl-β-cyclodextrin is preferably as described above in the compositions of the present invention.

In the process of the present invention, the addition of one or more pharmaceutically acceptable buffers, tonicity agents, preservatives, chelating agents, antioxidants, or anti-crystallizing agents may occur while bringing in intimate contact the Ifosfamide with the 2-hydroxylproplyl-β-cyclodextrin, or may be added to the Ifosfamide/2-hydroxylproplyl-β-cyclodextrin solution.

The solution may be sterilized and is preferably sterilized by filtering through a 0.2 μm filter. After sterilization, it is preferably to place the solution into sterile containers followed by purging of the air in the headspace of the containers with an inert gas such as nitrogen.

One embodiment of the present invention includes an aqueous Ifosfamide composition wherein 1 ml of the composition comprises 500 mg Ifosfamide, and 400 mg of 2-hydroxylpropyl-β-cyclodextrin.

Another embodiment of the present invention provides an aqueous Ifosfamide composition wherein 1 ml of the composition comprises 1000 mg Ifosfamide, and 50 mg of 2-hydroxylpropyl-β-cyclodextrin.

Yet another embodiment of the present invention provides an aqueous Ifosfamide composition wherein 1 ml of the composition comprises 50 mg Ifosfamide, and 100 mg of 2-hydroxylpropyl-β-cyclodextrin, and 0.3 mg Sodium dihydrogen phosphate, and 0.5 mg Disodium hydrogen phosphate.

DETAILED DESCRIPTION OF THE INVENTION

The present invention provides an Ifosfamide composition that is stable, clear, aqueous, sterile and ready to use. Compositions of the present invention may be concentrated, and they exhibit a reduced toxicity, as compared to currently available Ifosfamide compositions. Compositions of the present invention also have a reduced toxicity over and above the concomitant use of the uroprotective agent, Mesna.

The present invention provides an aqueous composition comprising Ifosfamide and 2-hydroxypropyl-β-cyclodextrin (HPBCD) that provides for a reduced toxicity, as compared to conventional Ifosfamide formulations (i.e. formulations not having HPBCD), both in the presence and absence of Mesna. Further, the present inventors have discovered that Ifosfamide (although a soluble drug) has an even greater solubility in HPBCD, which allows for the manufacture of concentrated Ifosfamide compositions, heretofore believed unachievable. It was believed that the highest concentration achievable in water was about 100 mg/ml. The present invention provides aqueous compositions of Ifosfamide at concentrations up to 1,100 mg/ml.

It is believed that the combination of Ifosfamide, HPBCD and water also provides stability to the Ifosfamide compositions of the present invention.

It is well known that the treatment with Ifosfamide is associated with serious side effects such as haemorrhagic cystitis. To counteract these side effects, Mesna is practically always administered with Ifosfamide injections. However, there are other side effects such as myelosuppression, cardiac arrythmias, CNS disturbances, nephrotoxicity, haematological and gastro-intestinal reactions which are not addressed by the co-administration of Mesna nor by the Ifosfamide compositions currently available.

Thus, the toxicity of the aqueous compositions of the present invention were evaluated against a conventional marketed Ifosfamide product (Holoxan™). The compositions of present invention when studied in Swiss albino mice showed lesser toxic effects such as convulsions, myelosuppressions, and hepatotoxicity. The mortality rate was found to be significantly less in animals treated with the compositions of the present invention compared to a conventional marketed product. $LD_{50}$ values demonstrate the reduced toxic nature of the compositions of the present invention. Such data is provided below in the Examples and Tables.

Not being bound by theory, it is believed that Ifosfamide, whole or in part, is complexed in the HPBCD cavity in an aqueous solution. On systemic administration, it is believed that the drug is released from the cavity in to the blood stream. The free drug and the drug-HPBCD complex will be in equilibrium and the metabolism of the free Ifosfamide shifts the equilibrium resulting in the release of free drug. Presence of Ifosfamide in complex form and optimum levels of free drug in the blood may prevent the interaction of Ifosfamide with healthy tissues and organs thereby preventing undesirable side effects.

In the present invention, Ifosfamide and HPBCD may form a synergistic combination that provides the reduced toxicity both in presence and absence of Mesna as shown by $LD_{50}$ values in mice and haemorrhagic cystitis studies in rats. The Ifosfamide compositions of the present invention having reduced toxicity are of advantage in the treatment of a variety of solid tumours including those of the cervix, endometrium, lung, ovary, testes and thymus as well as in sarcoma and in the treatment of Burkitts lymphoma.

The solubility of Ifosfamide in water is about 100 mg/ml. The present invention makes it possible to obtain an aqueous composition containing Ifosfamide in a concentration up to 1,100 mg/ml. Concentrated solutions offer additional advantages such as safety by virtue of less handling, and thus less exposure of clinicians to cytotoxic Ifosfamide during administration. Further, decreased handling provides an increase in the assurance of sterility.

Accordingly, in the present invention, in the aqueous compositions, Ifosfamide may be present at a concentration up to 1,100 mg/ml. Preferably the Ifosfamide is present at a concentration of 1–200 mg/ml, preferably at 10–100, preferably at 40–50 mg/ml, more preferably at 200–500 mg/ml and most preferably at 500–1,100 mg/ml.

Hydroxy propyl-β-cyclodextrin ("HPBCD") is a partially substituted poly(hydroxypropyl)ether of beta cyclodextrin. The hydroxypropyl groups are randomly substituted onto hydroxyl groups of the cyclodextrin and the amount of substitution is reported as average degree of substitution or number of hydroxypropyl groups per cyclodextrin. Alternatively, amount of substitution is reported as molar substitution (MS) or the average number of substitution per anhydroglucose unit in the ring of the cyclodextrin. Molar substitution can have an effect on the binding of guest molecules to HPBCD. At a low degree of substitution, binding is very similar to that of the unmodified beta-cyclodextrin. Increasing the molar substitution can lead to a weakened binding due to steric hindrance. HPBCD having molar substitution between 0.05 to about 2 is preferable. HPBCD having molar substitution between 0.3 to about 1.5 is preferred. HPBCD having molar substitution between 0.5 to about 1.2 is more preferred.

HPBCD may be present in the aqueous composition at a molar ratio of Ifosfamide to HPBCD at 100:0.1 to 1:300; preferably 100:0.25 to 1:100; more preferably 100:1 to 1:20. Other preferred molar ratio of Ifosfamide to HPBCD include 100:3.3 to 1:2.5. No significant changes in the toxicity profile were observed for compositions containing Ifosfamide:HPBCD in the ratios of 1:6 to 10:0.25.

In manufacturing concentrated aqueous Ifosfamide compositions of the present invention, the amount of HPBCD required varies with the concentration of Ifosfamide. Initially, as the concentration of Ifosfamide is increased, so too does the requirement for HPBCD increase. However, at certain point the requirement for HPBCD becomes less. At the higher end of Ifosfamide concentrations, HPBCD and water content is limited due to volume constraints. Therefore the ratio of Ifosfamide to HPBCD should be chosen, based on the teachings present herein, to allow for the manufacture of the concentrated Ifosfamide compositions of the present invention.

The pH of aqueous compositions of the present invention without any additives may be usually between 3.0–9.0. A preferably pH for the compositions of the present invention is between 5.0–8.0, but the pH may drop upon storage. The stabilisation of pH of the composition may require suitable buffers.

Aqueous compositions according to the present invention may also include pharmaceutically acceptable additives for the purposes of pH stabilisation, preservation (when the composition is diluted for administration), isotonicity adjustment, stabilisation against oxidation, chelating agents, anti-crystallising agents and other suitable excipients. Some of the pharmaceutically acceptable additives may be present in the aqueous solution to which the Ifosfamide and HPBCD are added and/or some of them may be added separately as a solution in water before making up the volume in the final composition.

Compositions in accordance with the present invention may, require buffers to adjust and stabilise the pH.

Suitable buffering agents for compositions of the present invention include, but are not limited to, Phosphate buffer, Citrate buffer, Glycine buffer, Histidine buffer containing any of the commonly used compounds or a mixture of compounds such as Citric acid, Sodium citrate, Potassium citrate, Glycine, hydrochloride, Phosphoric acid, Sodium phosphate, Disodium hydrogen phosphate, Sodium dihydrogen phosphate, Potassium phosphate, Dipotassium hydrogen phosphate, Potassium dihydrogen phosphate, Histidine hydrochloride, Sodium hydroxide, Potassium hydroxide and Hydrochloric acid. Preferably the buffer used comprises a mixture of Sodium dihydrogen phosphate and Disodium hydrogen phosphate.

Of the other conventional additives, suitable tonicity agents for compositions of the present invention include, but are not limited to, glycerin, sodium chloride, maltose, mannitol, dextrose and mixtures thereof.

Similarly, suitable preservatives for compositions of the present invention may include, but are not limited to, methyl hydroxy benzoic acid, propyl hydroxy benzoic acid, phenol, benzyl alcohol and sodium benzoate.

Compositions of the present invention may contain suitable chelating agents such as ethylenediaminetetraacetic acid (EDTA) and its salts and Desferoximine methane sulfonate (Desferal™).

Compositions of the present invention may also contain suitable antioxidants such as, ascorbic acid, sodium bisulfite, sodium metabisulfite, butylated hydroxy anisole and butylated hydroxy toluene.

Also, the composition of the present may contain substances such as Glycerin as anti-crystallizing agents.

The present invention also provides for a process of manufacturing aqueous Ifosfamide compositions. The process involves mixing Ifosfamide and HPBCD and water together. Aqueous solutions containing Ifosfamide and HPBCD are brought in intimate contact by stirring. Other methods of bringing the Ifosfamide and HPBCD in intimate contact include, but are not limited to, mixing, sonicating, heating and homogenising. Pharmaceutically acceptable additives such as buffers, tonicity agents, preservatives, chelating agents, antioxidants, anti-crystallizing agents as required by parenteral dosage form may be present in the aqueous solution to which the Ifosfamide and HPBCD is added. Alternatively, they can be added separately as a solution in water before making up the volume.

In preparing aqueous Ifosfamide compositions, to incorporate larger amounts of Ifosfamide, HPBCD is dissolved in minimum quantity of water and Ifosfamide is solubilized by intimate stirring. Pharmaceutically acceptable additives, if required by parenteral dosage form, are added as such or as solutions into the Ifosfamide-HPBCD solution. Finally the remaining quantity of water is added to makeup to the required volume followed by mixing to achieve a homogenous solution.

The composition may be rendered non-pyrogenic, if required, by passing through Tangential Flow Filtration System (TFF) before sterilisation.

In processes of the present invention the Ifosfamide and HPBCD may be present in the concentrations and ratios as described above with respect to the aqueous compositions.

Process of manufacturing the aqueous Ifosfamide compositions of the present invention further comprise sterilization of the composition. The compositions may be sterilized by known and acceptable methods. Preferably the composition is sterilised by filtering through a sterilising grade filter. Preferably, the solution is filtered through 0.2 μm sterilising grade filters.

After sterilization, it may be desirable to aseptically place the filtered solutions into sterile containers such as vials, ampoules, or plastic containers. Preferably, after aseptically placing the filtered solution into sterile containers, the air in the headspace of the containers is purged with an inert gas, such as nitrogen, and then the filled containers are sealed.

The following examples serve to illustrate aspects of the present invention and are meant in any way to limit the scope of the invention.

EXAMPLES

Ifosfamide used in these Examples was of parenteral grade complying with US Pharmacopoeial specifications. The HPBCD used was manufactured by Wacker Chemie having molar substitution per anhydroglucose unit by hydroxy propyl groups between 0.5 to 1.2. Equipment used were of conventional nature and the entire processing was performed in an area with a controlled environment. Water used in these Examples was of parenteral grade complying with "Water for Injection" specifications. All other additives used in these Examples were of parenteral grade.

Example I

Preparation of Ifosfamide 50 mg/ml Composition Containing 20% HPBCD in Water

The following composition was prepared by the procedure given below

| | | |
|---|---|---|
| i. | Ifosfamide | 10 gm |
| i. | HPBCD | 40 gm |
| ii. | Water | q.s. to 200 ml |

Weighed quantity of HPBCD was dissolved in 150 ml of water. Weighed quantity of Ifosfamide was added and mixed for 3 hours. The volume was made up to 200 ml with water and mixed. The resultant solution was filtered through a 0.2 μm filter and filled aseptically in sterile glass vials. The glass vials were closed under aseptic conditions with sterile Teflon™ coated rubber bungs and sealed using flip off seals.

The composition obtained in this Example was analyzed for Ifosfamide content by High Pressure Liquid Chromatography (HPLC) method and was found to contain 51.73 mg/ml of Ifosfamide. The composition had a pH of 6.5.

Example II

Stability of Composition of Example I

The composition obtained in Example I was subjected to long term Stability studies at 2–8° C. The stability data at the end of 24 months is shown in Table 1.

TABLE 1

Stability data of the composition of Example I

| Ifosfamide mg/ml | HPBCD % | Buffer | Initial % Ifosfamide content | 24 months at 2–8° C. % Ifosfamide content |
|---|---|---|---|---|
| 50 | 20% | — | 103.46 | 99.12 |

The above data shows insignificant drop in Ifosfamide content indicating a good stability.

Example III

Toxicity Study of Composition of Example I

The composition obtained in Example I was subjected to acute toxicity studies in mice. Experimental details are as follows.

| | |
|---|---|
| Animals used | Swiss albino mice of either sex |
| Weight range of animals | 20–22 gm |
| Number of groups | 10 |
| Number of animals per group | 10 |
| Acclimatization | One week under test conditions under controlled temperature and humidity |
| Test Materials | Ifosfamide Injection |
| Identity | Composition of Example I |
| Description | Clear colorless solution |
| Route of administration | Intravenous |
| Comparative material | Holoxan ™ (reconstituted) |
| Identity | Ifosfamide injection U.S.P. |
| Lot No. | G 220 |
| Manufacturing Date | October 2001 |
| Expiry Date | September 2003 |
| Description | Dry powder for reconstitution with water for injection |
| Strength | 40 mg/ml on reconstitution |
| Manufacturer | German Remedies Limited |
| Route of administration | Intravenous |

Both the drug solutions were suitably diluted with 5% Dextrose Injection and administered intravenously. Ifosfamide in the doses of 400 mg/kg, 500 mg/kg, 600 mg/kg, 700 mg/kg and 800 mg/kg body weight was administered in 10 different groups of animals, each group consisting of 10 animals.

The animals were kept under observation for 14 days and mortality recorded at the end of 7 days. The $LD_{50}$ dose (i.e. the dose that is lethal to 50% of animals) is shown in Table 2.

TABLE 2

$LD_{50}$ dose of Composition of Example I and Holoxan ™

| Composition | $LD_{50}$ (mg/kg Body weight) |
|---|---|
| Example I | 648.04 |
| Holoxan ™ | 562.16 |

The above data clearly indicates that composition of Example I is less toxic compared to the Conventional formulation.

Example IV

Preparation of Ifosfamide Composition Containing 10% HPBCD in Phosphate Buffer

The following composition was prepared by the procedure given below

| | | |
|---|---|---|
| i. | Ifosfamide | 10 gm |
| ii. | HPBCD | 20 gm |
| iii. | Disodium hydrogen phosphate | 0.1 gm |
| iv. | Sodium dihydrogen phosphate | 0.06 gm |
| v. | Water | q.s. to 200 ml |

Weighed quantities of Disodium hydrogen phosphate and Sodium dihydrogen phosphate were dissolved in 160 ml of water. Weighed quantity of HPBCD was added and dissolved slowly under stirring in this buffer solution. Weighed quantity of Ifosfamide was gradually added under stirring to the buffered HPBCD solution and mixed for 3 hours. The volume was made up to 200 ml with water and mixed. The resultant solution was filtered through a 0.2 μm filter and filled aseptically in sterile glass vials. The air in the headspace of the vials was purged with nitrogen and the glass vials were closed under aseptic conditions with sterile Teflon™ coated rubber bungs and sealed using flip off seals.

The composition obtained in this Example was analyzed for Ifosfamide content by High Pressure Liquid Chromatography (HPLC) method and was found to contain 50.23 mg/ml of Ifosfamide. The composition had a pH of 7.2.

Example V

Preparation of Ifosfamide 50 mg/ml Composition in Phosphate Buffer

To ascertain the toxicity reducing nature of HPBCD by toxicity studies a comparative composition containing Ifosfamide in buffer (without HPBCD) was prepared by the procedure given below.

| | | |
|---|---|---|
| i. | Ifosfamide | 10 gm |
| ii. | Disodium hydrogen phosphate | 0.1 gm |
| iii. | Sodium dihydrogen phosphate | 0.06 gm |
| iv. | Water | q.s. to 200 ml |

Weighed quantities of Disodium hydrogen phosphate and Sodium dihydrogen phosphate were dissolved in 180 ml of water. Weighed quantity of Ifosfamide was gradually added under stirring to the buffer solution and mixed for 3 hours. The volume was made up to 200 ml with water and mixed. The resultant solution was filtered through a 0.2 μm filter and filled aseptically in sterile glass vials. The air in the headspace of the vials was purged with nitrogen gas and the glass vials were closed under aseptic conditions with sterile Teflon™ coated rubber bungs and sealed using flip off seals.

The composition obtained in this Example was analyzed for Ifosfamide content by High Pressure Liquid Chromatography (HPLC) method and was found to contain 50.1 mg/ml of Ifosfamide. The composition had a pH of 6.5

Example VI

Acute Toxicity Study of the Compositions Prepared in Example IV and Example V

Experimental details are as follows.

| | |
|---|---|
| Animals used | Swiss albino mice of either sex |
| Weight range of animals | 20–22 gm |
| Number of groups | 25 |
| Number of animals per sub group | 8 |
| Acclimatization | One week under test conditions under controlled temperature and humidity. |

-continued

| | |
|---|---|
| Test Materials | Ifosfamide Injection |
| Identity | Composition of Example IV |
| Description | Clear colorless solution |
| Route of administration | Intravenous |
| Comparative material 1. | Ifosfamide Injection |
| Identity | Composition of Example V |
| Description | Clear colorless solution |
| Route of administration | Intravenous |
| Comparative material 2. | Holoxan ™ (reconstituted) |
| Uroprotective material | Uromitexan ™ |
| Identity | Mesna Injection |
| Lot No. | G 168 |
| Manufacturing Date | October 2001 |
| Expiry Date | September 2004 |
| Description | Clear & colorless solution for Intravenous Injection |
| Strength | 100 mg/ml |
| Manufacturer | German Remedies Limited |
| Route of administration | Intravenous |

(Details of Holoxan ™ are shown in Example III

The compositions obtained in Example IV and Example V were subjected to acute toxicity studies in mice. A conventional formulation, Holoxan™ was reconstituted as directed by the manufacturer and was used as a control. The doses of Ifosfamide selected for the study were 400 mg/kg, 500 mg/kg, 600 mg/kg, 700 mg/kg and 800 mg/kg body weight. The Ifosfamide solutions of compositions of Example IV, Example V and Holoxan™ were suitably diluted with 5% Dextrose Injection as such and also with Mesna at a dose of 20% of Ifosfamide dose and administered intravenously in 25 different groups of animals, each group consisting of eight animals.

The animals were kept under observation for 14 days and mortality recorded at the end of 7 days. The $LD_{50}$ values of compositions of Example IV, Example V, and Holoxan™ are shown in Table 3.

TABLE 3

The $LD_{50}$ values of compositions of Example IV, Example V and Holoxan ™

| Composition | HPBCD concentration | Buffer | Mesna Dose as % of Ifosfamide Dose | $LD_{50}$ (mg/kg Body weight) |
|---|---|---|---|---|
| Example IV | 10% | phosphate | — | 661.57 |
| Holoxan ™ | nil | nil | — | 562.16 |
| Example V | nil | phosphate | — | 566.00 |
| Example IV | 10% | phosphate | 20 | 669.54 |
| Holoxan ™ | nil | nil | 20 | 580.00 |

The above data clearly indicates that composition of Example IV is less toxic, both in presence and absence of Mesna, compared to the conventional formulation, as well as Ifosfamide in buffered solution.

Example VII

Repeat Dose Toxicity Studies of Composition of Example IV

The composition obtained in Example IV along with conventional formulation Holoxan™ were subjected to repeat dose toxicity study in mice to evaluate the effect of Ifosfamide compositions on haematological and biochemical parameters. Experimental details are as follows.

| | |
|---|---|
| Animals used | Swiss albino mice of either sex |
| Weight range of animals | 20–22 gm |
| Number of groups | 7 |
| Number of animals per group | 10 |
| Acclimatization | One week under test conditions under controlled temperature and humidity. |
| Test Materials | Composition of Example IV |
| Comparative material | Holoxan ™ |
| Uroprotective material | Uromitexan ™ |

(The details of Holoxan ™ and Uromitexan ™ are given in Example VI)

The animals were injected Ifosfamide along with Mesna (as 20% of Ifosfamide Dose) at daily doses of 80 mg/kg, 100 mg/kg and 120 mg/kg, intravenously for seven days. The untreated group was used as a control. The animals were observed during the study period of 14 days for mortality, haematological and biochemical changes. The total WBC count was done before and after treatment with composition of Example IV and Holoxan™. The values are shown in Table 4.

TABLE 4

The total WBC count of animals treated with composition of Example IV and Holoxan ™

| Dose (mg/kg body weight) | | Total WBC (cells/microliter) ± SEM | | | | | |
|---|---|---|---|---|---|---|---|
| | | Example IV | | Holoxan ™ | | Control | |
| Ifosfamide | Mesna | Pre treatment | Post treatment | Pre treatment | Post treatment | Pre treatment | Post treatment |
| 80 | 16 | 6220.00 ± 631.73 | 3170.00 ± 478.21 | 4870.00 ± 310.94 | 1840.00 ± 131.83 | 7920.00 ± 539.93 | 10980.0 ± 666.65 |
| 100 | 20 | 5760.00 ± 435.44 | 6440.00 ± 1764.2 | 5980.00 ± 806.77 | 2220.00 ± 237.02 | | |
| 120 | 24 | 5900.00 ± 481.91 | 4420.00 ± 1102.0 | 8150.00 ± 904.61 | 1362.50 ± 301.15 | | |

The animals treated with Example IV and Holoxan™ showed reduction in total WBC count. However, animals treated with Holoxan™ showed severe leucopoenia compared to composition of Example IV. This indicates a less toxic nature of composition of Example IV.

To study the effect of composition of Example IV and Holoxan™ on Liver function, the Serum Glutamate Oxaloacetate Transaminase (SGOT) levels of treated and untreated control group were analysed. The SGOT levels of treated and untreated control groups are shown in Table 5.

TABLE 5

The average SGOT levels of animals treated with composition of Example IV, Holoxan ™ and untreated control

| Dose of Ifosfamide (mg/kg body weight) | Dose of Mesna (mg/kg body weight) | SGOT level (U/L) | | |
|---|---|---|---|---|
| | | Example IV | Holoxan ™ | Control |
| 80 | 16 | 129.15 | 158.50 | 136.4 |
| 100 | 20 | 147.8 | 299.65 | |
| 120 | 24 | 164.25 | 309.15 | |

As per the above data, the elevation of SGOT levels in animals treated with Example IV was slightly higher than that of control group, whereas in animals treated with Holoxan™ increase in SGOT values was highly significant. This indicates reduced hepatotoxic nature of composition of Example IV.

Example VIII

Hemorrhagic Cystitis Studies of Composition IV

The composition obtained in Example IV along with conventional formulation Holoxan™ were subjected to Hemorrhagic cystitis studies in rats to evaluate their bladder toxicity. Experimental details are as follows.

| | |
|---|---|
| Animals used | Wistar rats of either sex |
| Weight range of animals | 100–150 gm |
| Number of groups | 9 |
| Number of animals per group | 2 |
| Acclimatization | One week under test conditions under controlled temperature and humidity. |
| Test Materials | Composition of Example IV |
| Comparative material. | Holoxan ™ |
| Uroprotective material | Uromitexan ™ |

(The details of Holoxan ™ and Uromitexan ™ are given in Example VI)

Study Design

Animals were divided into 9 groups and each group comprised two animals. Ifosfamide alone and with Mesna was administered via the intravenous route at doses of 400 mg/kg and 500 mg/kg bodyweight. The group treated with Dextrose Injection was used as a control.

The animals were sacrificed 24 hours after injection. The urinary bladders of all the animals were collected and were fixed in 10% formalin for 48 hours. Histopathological slides of the organ were prepared and subjected to microscopic examination. Table 6 depicts the evaluation results on hemorrhagic cystitis of two formulations of Ifosfamide.

TABLE 6

Scoring of hemorrhagic cystitis

| | | | Score | |
|---|---|---|---|---|
| Sl no | Ifosfamide Dose | Mesna Dose | Example IV | Holoxan ™ |
| 1 | 400 | — | 1+ | 2+ |
| 2 | 400 | — | N | 3+ |
| 3 | 500 | — | 1+ | 3+ |
| 4 | 500 | — | 1+ | 1+ |
| 5 | 400 | 80 | N | 1+ |
| 6 | 400 | 80 | N | 1+ |
| 7 | 500 | 100 | N | 1+ |
| 8 | 500 | 100 | N | 2+ |

N: Normal
1+: Mild hemorrhagic cystitis
2+: Moderate hemorrhagic cystitis with or without epithelial atypia
3+: Severe hemorragic cystitis with or without epithelial atypia Results:

| | |
|---|---|
| Holoxan | moderate to severe hemorrhagic cystitis |
| Holoxan with Mesna | mild to moderate hemorrhagic cystitis |
| Example IV | mild to moderate hemorrhagic cystitis |
| Example IV with Mesna | No hemorrhagic cystitis |

The above findings conclusively proved that the composition of Example IV has less bladder toxicity than the conventional formulation Holoxan™.

Example IX

Stability Study of Composition of Example IV

The composition obtained in Example IV was subjected to stability studies at 2° C.–8° C. The samples at the end of 6 and 12 months were analysed by HPLC method. The data is shown in Table 7.

TABLE 7

Stability data of composition of Example IV

| Storage condition | Description | % Ifosfamide content |
|---|---|---|
| Initial | Clear, colourless liquid | 50.2 mg/ml |
| 2° C.–8° C. - 6 M | Clear, colourless liquid | 50.9 mg/ml |
| 2° C.–8° C. - 12 M | Clear, colourless liquid | 49.1 mg/ml |

The above data shows insignificant drop in Ifosfamide content at 2° C.–8° C. indicating good stability.

Numerous compositions of the present invention comprising different concentrations of Ifosfamide and HPBCD are shown in the Table 8.

TABLE 8

Other embodiments of the present invention

| | Example | | | | | | |
|---|---|---|---|---|---|---|---|
| Ingredients | X | XI | XII | XIII | XIV | XV | XVI |
| Ifosfamide | 10.0 g | 10.0 g | 10.0 g | 20.0 g | 100 g | 100 g | 200 g |
| HPBCD | 40.0 g | 80.0 g | 20.0 g | 40.0 g | 40.0 g | 80.0 g | 10.0 g |
| Disodium hydrogen phosphate | 0.1 g | 0.1 g | — | 0.1 g | — | — | — |
| Sodium dihydrogen phosphate | 0.06 g | 0.06 g | — | 0.06 g | — | — | — |
| Water to make up the volume | qs to 200 ml | qs to 200 ml | qs to 200 ml | qs to 200 ml | qs to 200 ml | qs to 200 ml | qs to 200 ml |
| Ifosfamide concentration | 50 mg/ml | 50 mg/ml | 50 mg/ml | 100 mg/ml | 500 mg/ml | 500 mg/ml | 1000 mg/ml |

The compositions shown in Table 8 were prepared by the procedures given below.

Example X

Ifosfamide (10 g) and HPBCD (40 g), Disodium hydrogen phosphate (0.1 gm) and Sodium hydrogenphosphate (0.06 gm) were taken in a volumetric flask of 200 ml capacity. Water for injection was slowly added into it with intermittent mixing to get 200 ml clear homogenous solution. The resultant solution was passed through sterile 0.2 µm filter and filled aseptically in sterile 10 ml glass vials. The air in the headspace was purged with nitrogen gas and the glass vials were closed under aseptic conditions with sterile Teflon™ coated rubber bungs and sealed using flip-off seals.

Example XI

Ifosfamide (10 gm) and HPBCD (80 gm), Disodium hydrogen phosphate (0.1 gm in 10 ml of water) and Sodium hydrogen phosphate (0.06 gm in 10 ml of water) were taken in a volumetric flask of 200 ml capacity. Water for injection was slowly added into it with intermittent mixing to get 200 ml clear homogenous solution. The resultant solution was passed through sterile 0.2 µm filter and filled aseptically in sterile 10 ml glass vials. The air in the headspace was purged with nitrogen gas and the glass vials were closed under aseptic conditions with sterile Teflon™ coated rubber bungs and sealed using flip-off seals.

Example XII

Weighed quantity of HPBCD was dissolved in 40 ml of water. To the concentrated solution of HPBCD, Ifosfamide was added gradually and the mixture was stirred at a moderate speed for 1 hour. The clear solution was then diluted to 200 ml with water. The resultant solution was filtered through 0.2 µm filter and filled aseptically in sterile glass vials. The air in the headspace of the vials was purged with nitrogen gas and the glass vials were closed under aseptic conditions with sterile Teflon™ coated rubber bungs and sealed using flip off seals.

Example XIII

The compositions were prepared by following the procedure of Example IV using the components in the amounts mentioned in Table 8.

Example XIV

Weighed quantity of HPBCD was dissolved in 80 ml of water. To the concentrated solution of HPBCD, Ifosfamide was added gradually and dissolved by stirring. The volume was made up to 200 ml with water and mixed. The resultant solution was filtered through 0.2 µm filter and filled aseptically in sterile glass vials. The air in the headspace of the vials was purged with nitrogen gas and the glass vials were closed under aseptic conditions with sterile Teflon™ coated rubber bungs and sealed using flip off seals. The composition in this example was analysed for Ifosfamide content by HPLC as was found to contain 500.3 mg/ml of Ifosfamide.

Example XV

The composition was prepared by following the procedure of Example XIV using the components in the amounts mentioned in Table 8. The composition in this example was analysed for Ifosfamide content by HPLC as was found to contain 500.28 mg/ml of Ifosfamide.

Example XVI

Ifosfamide (200 gm) and HPBCD (10 gm) were taken in a volumetric flask of 200 ml capacity. Water for injection was slowly added into it with intermittent mixing to get a 200 ml clear homogenous solution. The resultant solution was filtered through 0.2 μm filter and filled aseptically in sterile glass vials. The air in the headspace of the vials was purged with nitrogen gas and the glass vials were closed under aseptic conditions with sterile Teflon™ coated rubber bungs and sealed using flip off seals. The composition in this example was analysed for Ifosfamide content by HPLC as was found to contain 1025.5 mg/ml of Ifosfamide.

We claim:

1. An aqueous Ifosfamide composition having reduced toxicity for parenteral administration comprising Ifosfamide and 2-hydroxylpropyl-β-cyclodextrin, wherein the Ifosfamide is present at a concentration up to 1,100 mg/ml.

2. The composition of claim 1, wherein the Ifosfamide is present at 1–200 mg/ml.

3. The composition of claim 1, wherein the Ifosfamide is present at 10–100 mg/ml.

4. The composition of claim 1, wherein the Ifosfamide is present at 40–50 mg/ml.

5. The composition of claim 1, wherein the Ifosfamide is present at 200–500 mg/ml.

6. The composition of claim 1, wherein the Ifosfamide is present at 500–1,000 mg/ml.

7. The composition of claim 1, wherein the concentration of Ifosfamide is greater than 1,000 mg/ml.

8. The composition of claim 1, wherein the 2-hydroxypropyl-β-cyclodextrin has a molar substitution by hydroxy propyl groups of 0.05–2.

9. The composition of claim 1, wherein the 2-hydroxypropyl-β-cyclodextrin has a molar substitution by hydroxy propyl groups of 0.3–1.5.

10. The composition of claim 1, wherein the 2-hydroxypropyl-β-cyclodextrin has a molar substitution by hydroxy propyl groups of 0.5–1.2.

11. The composition of claim 1 wherein the molar ratio of Ifosfamide to 2-hydroxypropyl-β-cyclodextnn is 100:0.1–1:300.

12. The composition of claim 1, wherein the molar ratio of Ifosfamide to 2-hydroxypropyl-β-cyclodextrin is 100:0.25–1:100.

13. The composition of claim 1, wherein the molar ratio of Ifosfamide to 2-hydroxypropyl-β-cyclodextrin is 100:1–1:20.

14. The composition of claim 1, wherein the molar ratio of Ifosfamide to 2-hydroxypropyl-β-cyclodextrin is 100:3.3–1:2.5.

15. The composition of claim 1, further comprising pharmaceutically acceptable buffers, tonicity agents, preservatives, chelating agents, antioxidants, or anti-crystallizing agents.

16. The composition of claim 15, wherein the pH of the composition is between 3.0–9.0.

17. The composition of claim 16, wherein the pH of the composition is between 5.0–8.0.

18. The composition of claim 15, wherein the buffering agent is selected from the group consisting of Sodium dihydrogen phosphate, Disodium hydrogen phosphate. Dipotassium hydrogen phosphate, Potassium dihydrogen phosphate, Histidine HCl, Sodium Hydroxide, Phosphoric acid, and Hydrochloric acid and mixtures thereof.

19. The composition of claim 18, wherein the buffering agent is a mixture of Sodium dihydrogen phosphate and Disodium hydrogen phosphate.

20. A process for the preparation of an aqueous Ifosfamide composition comprising bringing in intimate contact Ifosfamide, 2-hydroxypropyl-β-cyclodextrin, and water to form an aqueous Ifosfamide/2-hydroxyl-β-cyclodextrin solution.

21. The process of claim 20, wherein the Ifosfamide is present at a concentration of 1–200 mg/ml.

22. The process of claim 20, wherein the Ifosfamide is present at a concentration of 10–100 mg/ml.

23. The process of claim 20, wherein the Ifosfamide is present at a concentration of 40–50 mg/ml.

24. The process of claim 20, wherein the Ifosfamide is present at a concentration of 200–500 mg/ml.

25. The process of claim 20, wherein the Ifosfamide is present at a concentration of 500–1,000 mg/ml.

26. The process of claim 20, wherein the Ifosfamide is present at a concentration of greater than 1,000 mg/ml.

27. The process of claim 20, wherein the 2-hydroxypropyl-β-cyclodextrin has a molar substitution by hydroxy propyl groups of 0.5–1.2.

28. The process of claim 20, wherein the molar ratio of Ifosfamide to 2-hydroxypropyl-β-cyclodextrin is 100:0.1–1:300.

29. The process of claim 20, wherein the molar ratio of Ifosfamide to 2-hydroxypropyl-β-cyclodextrin is 100:0.25–1:100.

30. The process of claim 20, wherein the molar ratio of Ifosfamide to 2-hydroxypropyl-β-cyclodextrin is 100:1–1:20.

31. The process of claim 20, wherein the molar ratio of Ifosfamide to 2-hydroxypropyl-β-cyclodextrin is 100:3.3–1:2.5.

32. The process of claim 20, further comprising adding one or more pharmaceutically acceptable buffers, tonicity agents, preservatives, chelating agents, antioxidants, or anti-crystallizing agents while bringing in intimate contact the Ifosfamide with the 2-hydroxylproplyl-β-cyclodextrin.

33. The process of claim 20, further comprising adding one or more pharmaceutically acceptable buffers, tonicity agents, preservatives, chelating agents, antioxidants, or anti-crystallizing agents to the Ifosfamide/2-hydroxylproplyl-β-cyclodextrin solution.

34. The process of claim 32, further comprising sterilization by filtering through a sterile 0.2 μm filter.

35. The process of claim 33, further comprising aseptically placing the solution into sterile containers followed by purging of air in the containers with an inert gas, followed by sealing the containers.

36. An aqueous Ifosfamide composition according to claim 1 wherein each ml of the composition comprises:
   Ifosfamide: 500 mg; and
   2-hydroxylpropyl-β-cyclodextrin: 400 mg.

37. An aqueous Ifosfamide composition according to claim 1 wherein each ml of the composition comprises:
   Ifosfamide: 1000 mg; and
   2-hydroxylpropy-β-cyclodextrin: 50 mg.

38. An aqueous Ifosfamide composition according to claim 1 wherein each ml of the composition comprises:
   Ifosfamide: 50 mg;
   2-hydroxylpropyl-β-cyclodextrin: 100 mg;
   Sodium dihydrogen phosphate: 0.3 mg; and
   Disodium hydrogen phosphate: at 0.5 mg.

* * * * *